United States Patent [19]

Drewlow

[11] Patent Number: Plant 7,098

[45] Date of Patent: Jan. 9, 1990

[54] IMPATIENS PLANT NAMED RADIANCE

[75] Inventor: Lyndon W. Drewlow, Ashtabula, Ohio

[73] Assignee: Mikkelsens, Inc., Ashtabula, Ohio

[21] Appl. No.: 308,817

[22] Filed: Feb. 9, 1989

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

An Impatiens plant named Radiance, having large red flowers, excellent self-branching and floriferousness, good trailing habit, variegated leaves, and excellent tolerance to both high and low temperatures.

1 Drawing Sheet

The present invention relates to a new and distinctive cultivar of Impatiens plant, botanically known as Impatiens, and known by the cultivar name Radiance. The new cultivar was developed by me through controlled breeding by crossing Mikkelsen Seedling No. 86-185-1 (seed parent) with Mikkelsen Seedling No. 86-203-4 (pollen parent). Asexual reproduction by terminal or stem cuttings has shown that the unique features of this new impatiens are stabilized and are reproduced true to type in successive propagations.

The following characteristics distinguish the new impatiens from both its parent varieties and other cultivated impatiens of this type known and used in the floriculture industry. Certain characteristics are more meaningful by reference to known cultivars. References are made to Cosmos, U.S. Pat. No. P. 5,153; Pulsar, U.S. Pat. No. P. 5,783; Zenith, U.S. Pat. No. P. 5,804, and Mimas.

1. Radiance is a deep cherry-red in flower color while Cosmos is ligher in color, Pulsar has more red in the flower, and Mimas is more cherry lilac in color.

2. The anther hood of Radiance has a moderate amount of reddish coloration, while Cosmos only has a trace and Pulsar and Mimas are solid reddish except for the top area.

3. Radiance is similar in growth to Cosmos with both having semi-trailing habits making them excellent for hanging baskets. Pulsar is a more upright compact growing plant, and Mimas is a totally upright plant with a more open habit.

4. Radiance has large flowers similar in size to Zenith, with Pulsar, Mimas and Cosmos having much smaller flowers.

5. Leaf coloration of Radiance is a deep green which is similar to Cosmos, while Zenith has a lighter green leaf, and Pulsar and Mimas have red-green leaves.

6. The leaf shape of Cosmos is narrower than Radiance, with Pulsar, Zenith and Mimas all having broader leaves. The leaves of Pulsar are shorter in length than Radiance, with Mimas having longer leaves, and Cosmos and Zenith having similar length leaves.

7. Midrib of leaves of Radiance has more red pigmentation than Cosmos, but not as much as Pulsar and Mimas.

8. Radiance has the deepest reddish purple spur of the flower, with Mimas, Cosmos and Pulsar all having lighter spurs, in that order.

9. Red pigmentation in the stems of Radiance is more than Zenith but not as much as Cosmos, Pulsar, and Mimas, with Mimas having the largest amount.

10. Radiance is very floriferous, and flowers early from planted cuttings.

11. In the Radiance flower the two lower petals are larger than the upper petal, while in Cosmos those three petals are of equal size, and in Pulsar, Zenith and Mimas the upper petal is the largest.

The accompanying colored photograph is a top perspective view showing the overall appearance of Radiance, with colors being as true as it is reasonably possible to obtain in a colored reproduction of this type. The photograph was taken in late June with the plant being grown in a greenhouse.

The following is a detailed description of Radiance based on plants produced under commercial practices in Ashtabula, Ohio under both greenhouse and outdoor growing conditions. Color references are made to The Royal Horticultural Society Colour Chart except where general terms of ordinary dictionary significance are used.

Parentage: A controlled cross between Mikkelsen Seedling No. 86-185-1 and Mikkelsen Seedling No. 86-203-4.

Propagation:

*Type cutting.*—Stem cutting 15 mm long will develop to 4 to 5 cm long in 18 to 21 days.

*Time to root.*—8 to 10 days at 23° C. summer, and 10 to 12 days at 20° C. winter.

*Rooting habit.*—Heavy, fibrous.

Plant description:

*Form.*—Semi-compact, self-branching, vigorous growing, symmetrically mounded, flowering herb.

*Habit of growth.*—Mounded with flowering over the top of the foliage; vigorous, continuous flowering; heavy self-branching; stems slightly trailing.

*Foliage.*—Dark green leaves with green venation; cream central variegation is present approximately two-thirds the way up the leaf; on immature leaves variegation starts as yellowish green color. On mature leaves there is small yellowish green band between cream area and dark green area. (1) Size: 10 to 12 cm long and 3 to 3.5 cm wide at maturity. Environment can affect the size of the leaf. (2) Shape: Oblanceolate with acute apex and base. (3) Texture: Both upper and lower surfaces glabrous. (4) Margin: Entire and finely ciliated. (5) Color: Young foliage, top side: 137A with center variegation 144A. Under side: 137C. Mature foliage, top side: 147A with yellow-green with central variegation 11C and band 144A. Under side: 148B. (6) Venation: Pinnate, green in color.

Flowering description:

*Flowering habits.*—Flowers continuously from leaf whorl in progressively orderly manner with usually one flower per leaf axil but two on occasion. The whorl above starts to open about the time the last flowers appear on the whorl below. It takes 5 to 7 days from bud to bloom, and flowers last two weeks or longer depending on the environment.

*Natural flowering season.*—Indeterminant and continuous. Quantity of flowering increases with increasing levels of light.

*Flower buds.*—Ellipsoidal, flowers perfect; reddish spurs (last 1–2 mm is green) up to 3.5 cm long on mature buds with throat behind ovary and originating from the major sepal.

*Flowers borne.*—On individual pedicels from whorls of usually seven leaves, flowering progressively around the whorl as buds and leaves develop; most leaf axils have only one flower, but occasionally two.

*Quantity of flowers.*—Many large flowers; flower development is continuous so that tight buds to mature blooms are visible at the same time. Self-branching habit makes plant floriferous as each branch has flowers.

*Petals.*—(1) Shape: Heart shaped with two lower petals the largest. (2) Color: Top side in summer when opening, 53C fading to 63A to 63B; under side 63B. (3) Number of petals: Five (5) in number. (4) Size of flowers: 6.0 to 6.5 cm in diameter.

*Reproductive organs.*—(1) Stamens: Five (5) in number. (a) Anther Shape: Hooded, color cream with reddish purple cast. (b) Pollen color: Cream. (2) Pistels (a) Stigma shape: Five (5) in number, segmented, column shaped; color, whitish. (b) Style color: Cream. (c) Ovaries: Five (5) in number, size 5 mm, color, green.

Disease resistance: No significant disease or insect problems noted to date.

Other characteristics: Radiance has shown tolerance to high temperatures and sunlight without stopping blooming or incurring burn. The new cultivar is highly self-branched and floriferous, with flowers covering the plant canopy. It also has its ability to tolerate low temperatures (40°–50° F.) both in spring and fall which extends the flowering season.

I claim:

1. A new and distinct cultivar of Impatiens plant named Radiance, as illustrated and described.

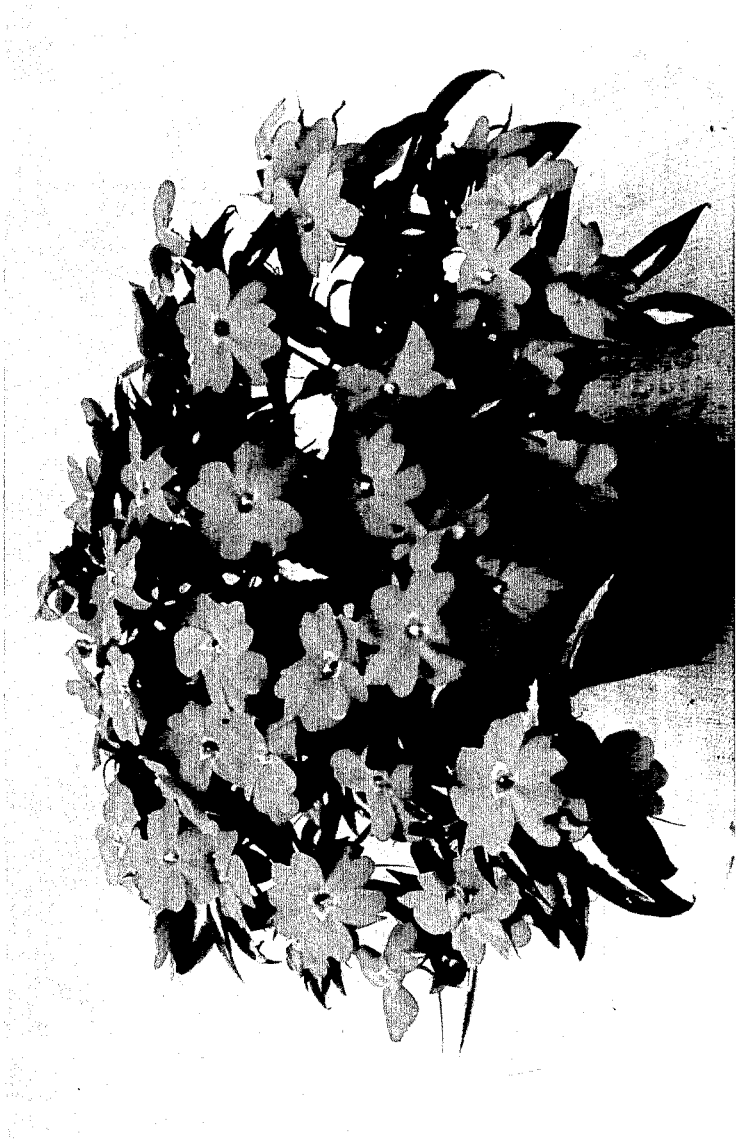

* * * * *